(12) United States Patent
Frotscher et al.

(10) Patent No.: US 8,738,301 B2
(45) Date of Patent: May 27, 2014

(54) METHOD FOR GAS ANALYSIS OF ON-LOAD TAP CHANGERS

(75) Inventors: Rainer Frotscher, Regenstauf (DE); Ralf Hartwig, Berlin (DE)

(73) Assignee: Maschinenfabrik Reinhausen GmbH, Regensburg (DE)

( * ) Notice: Subject to any disclaimer, the term of this patent is extended or adjusted under 35 U.S.C. 154(b) by 180 days.

(21) Appl. No.: 13/140,846

(22) PCT Filed: Apr. 15, 2010

(86) PCT No.: PCT/EP2010/002306
§ 371 (c)(1),
(2), (4) Date: Jul. 25, 2011

(87) PCT Pub. No.: WO2010/127759
PCT Pub. Date: Nov. 11, 2010

(65) Prior Publication Data
US 2012/0041688 A1    Feb. 16, 2012

(30) Foreign Application Priority Data
May 6, 2009    (DE) .......................... 10 2009 021 036

(51) Int. Cl.
*G06F 19/00*    (2011.01)
(52) U.S. Cl.
USPC ............. 702/24; 702/130; 702/136; 702/185; 323/255; 323/258; 323/260; 323/341; 73/19.1; 73/23.41; 73/23.2
(58) Field of Classification Search
USPC ........... 702/24, 57, 58, 60, 64, 130, 136, 183; 323/255, 258, 260, 324; 73/19.01, 73/19.02, 19.1, 23.41, 23.2, 61.55
See application file for complete search history.

(56) References Cited

U.S. PATENT DOCUMENTS

| 4,502,320 A | * | 3/1985 | Sakai et al. ................... 73/19.1 |
| 6,157,196 A | * | 12/2000 | Bengtsson et al. ............ 324/420 |
| 7,089,145 B2 | * | 8/2006 | Stenestam et al. ............ 702/130 |

(Continued)

FOREIGN PATENT DOCUMENTS

| DE | 218465 B | 2/1985 |
| JP | 08031669 A | * | 2/1996 |

OTHER PUBLICATIONS

F. Jakob et al; Use of gas concentration ratios to interpret ITC . . . ; IEEE (2003); pp. 301-304.

(Continued)

*Primary Examiner* — Carol S Tsai
(74) *Attorney, Agent, or Firm* — Lucas & Mercanti, LLP

(57) ABSTRACT

The present invention relates to a method for quantitatively analyzing gases as a monitor for on-load tap changers. The general inventive concept lies in selecting particular characteristic gases allowing an indirect subsequent association and a dimension for aging effects, excessive discharge, and/or heating of the on-load tap changer; measuring said characteristic gases, formed during the operation of the tap changer in the insulating oil thereof, at particular time intervals; forming indicative quotients from the measured values of the defined gases, said quotients allowing direct conclusions about aging effects, excessive discharge, and/or heating; displaying trends from a comparison of the currently derived value of each quotient to the most recently derived value for the same quotient; and inferring warnings for aging effects, excessive discharge, and/or heating if the corresponding quotients tend to change significantly over time or in the course of the switch changes made.

4 Claims, 3 Drawing Sheets

(56) References Cited

U.S. PATENT DOCUMENTS

Figure 1:
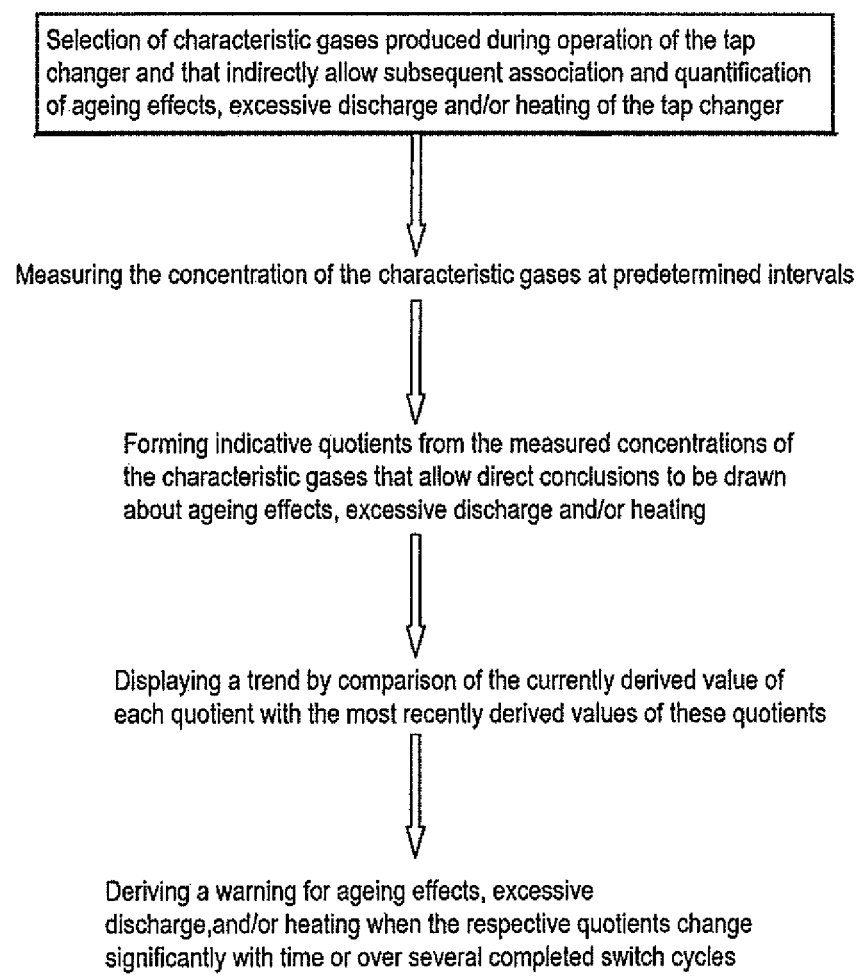

| | | | |
|---|---|---|---|
| 7,272,516 B2 * | 9/2007 | Wang et al. | 702/60 |
| 7,323,852 B2 * | 1/2008 | Hoffman | 323/258 |
| 8,207,457 B2 * | 6/2012 | Twibell et al. | 200/11 TC |
| 8,347,687 B2 * | 1/2013 | Cunningham | 73/19.11 |
| 2004/0021449 A1 * | 2/2004 | Stenestam et al. | 323/255 |
| 2009/0200290 A1 * | 8/2009 | Cardinal et al. | 219/488 |
| 2010/0005856 A1 * | 1/2010 | Cunningham | 73/23.41 |

OTHER PUBLICATIONS

M. Duval; The duval triangle for load tap changers, . . . ; IEEE (2008); vol. 24; No. 6; pp. 22-29.

Duval, M. "The Duval Triangle for Load Tap changers . . . " IEEE Elec. Ins. Mag., vol. 11 No. 8 Nov. 1, 2009 ISSN 0883-07554.

Jakob, F "Use of Gas Concentration Ratios . . . " Proc. of Elec. Ins Conf. Sep. 23, 2003 ISBN 978-0-7803-7935-0 p. 301-304.

* cited by examiner

METHOD FOR GAS ANALYSIS OF ON-LOAD TAP CHANGERS

CROSS REFERENCE TO RELATED APPLICATIONS

This application is the US national phase of PCT application PCT/EP2010/002306, filed 15Apr. 2010, published 11Nov. 2010 as WO2010/127759, and claiming the priority of German patent application 102009021036.9 itself filed 6May 2009, whose entire disclosures are herewith incorporated by reference.

The invention relates to a method of quantitatively analyzing gases, in particular a monitoring system for on-load tap changers.

Tap changers have been used in large numbers worldwide for many years for the uninterrupted changeover between different winding taps of variable-step transformers. Such tap changers usually consist of a selector for off-load selection of the particular winding tap of the variable-step transformer in which the changeover is to take place and an on-load changeover switch for actually changing over from the previous to the newly pre-selected winding tap. The on-load changeover switch also usually has switching contacts and resistor contacts. Here, the switching contacts are used to directly connect the respective winding tap to the outgoing load cable, and the resistor contacts for short-term connection, i.e. bridging by one or more transition resistors. However, the developments of recent years have led away from on-load changeover switches with mechanical switching contacts. Instead, vacuum switching cells or even thyristors as switching elements are increasingly used.

Regardless of the changeover principle, a tap changer is a mechanically and electrically stressed device that, measured against its actual value, almost always results in very high consequential damage in the power supply network in the event of a technical failure. Consequently, it is in the interests of power providers and power plant operators to detect possible damage to the tap changer as early as possible and also to assign a firm cause of the fault. A reliable method has not previously been disclosed.

A method of monitoring oil-insulated high-voltage devices, in particular oil transformers, is described in DD 218465. This method enables damage to be identified at an early stage by detecting damage-specific gas components, for example $CH_4$, $C_2H_6$, $C_2H_4$, $C_3H_8$, $C_3H_6$, in the trace concentration range by continuously recording a plurality of gas components of this kind of the free gases that exist in solution equilibrium with the insulating oil in an oil tank.

This method is only mentioned by way of example and is representative of a whole range of further known methods that, however, are concerned exclusively with the early identification of possible damage to power transformers. However, it is expressly not possible to transfer the knowledge of gas-in-oil analyses or dissolved gas analysis (DGA) obtained from these disclosures to a monitoring system especially for a tap changer. Different fundamental conditions from those in a power transformer prevail in a tap changer, as a tap changer requires components such as transition resistors and mechanically moving contacts that can be a crucial factor for occurring faults and that a power transformer precisely does not need.

The object of the invention is accordingly to provide a method of quantitatively analyzing gases as a monitoring system for on-load tap changers with which reliable conclusions relating to imminent damage to the tap changer can be drawn at an early stage. Furthermore, it is an object of the invention to ascribe these conclusions to a particular fault cause.

According to the invention, this object is achieved by a method with the method steps of the first patent claim. The dependent claims relate to particularly advantageous improvements of the method according to the invention.

The general inventive concept lies in selecting particular characteristic gases that allow an indirect subsequent association and quantification of ageing effects, excessive discharge, and/or heating of the tap changer; measuring the characteristic gases formed during the operation of the tap changer in the insulating oil thereof at particular time intervals; forming from the measured values of the defined gases indicative quotients allowing direct conclusions to be drawn about ageing effects, excessive discharge, and/or heating; displaying trends from a comparison of the currently derived value of each quotient with the most recently derived value of the same quotient; and deriving warnings for ageing effects, excessive discharge, and or heating therefrom if the corresponding quotients tend to change significantly over time or in the course of the switching operations carried out.

Although for all intents and purposes individual method steps of the inventive concept are known per se, the state of knowledge disclosed in the prior art has simply not been sufficient to provide a monitoring system for a tap changer. In fact, numerous deliberations and laboratory tests have been necessary to further develop the known method steps in such a way that an inventive method according to the characteristics of the first patent claim could be specified. In this context, technical specifics of tap-changer technology have required particular inventive deliberations in the development of indicative quotients that now allow conclusions to be drawn about ageing effects, excessive discharge and/or heating in the tap changer; this has not previously been possible. In the invention, particular characteristic gases that occur in the tap changer are accordingly linked to form quotients that are assigned to particular physical phenomena.

In a particularly advantageous manner, the derived quotients are displayed in a two-dimensional Cartesian coordinate system in which the abscissa is formed by a unit that can be measured in time. It is also conceivable to take the progressive number of switching operations completed by the tap changer as the time unit. In this representation the indicative quotients can be displayed in a particularly simple manner against a time axis, significant changes in the appropriate quotients being represented by deviations in the diagram image.

In a further modified improvement of the invention, a triangular coordinate system with three axes can be used to represent the quotients, as is the case, for example, with the "Duval Triangle" that is known per se. In this chosen form, indicative quotients are displayed with respect to one another in a is relative percentage display.

Figure 2:
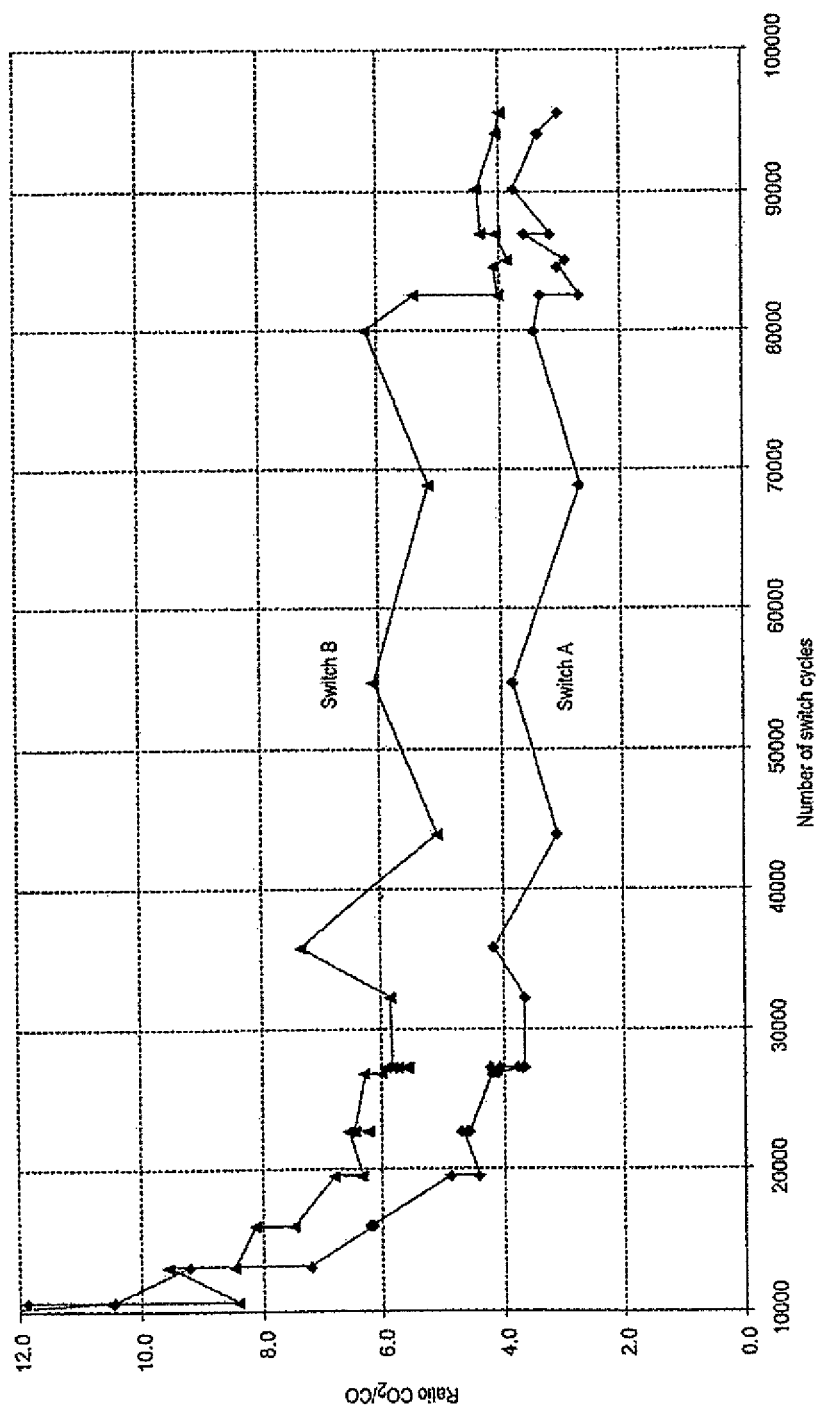
Figure 3:
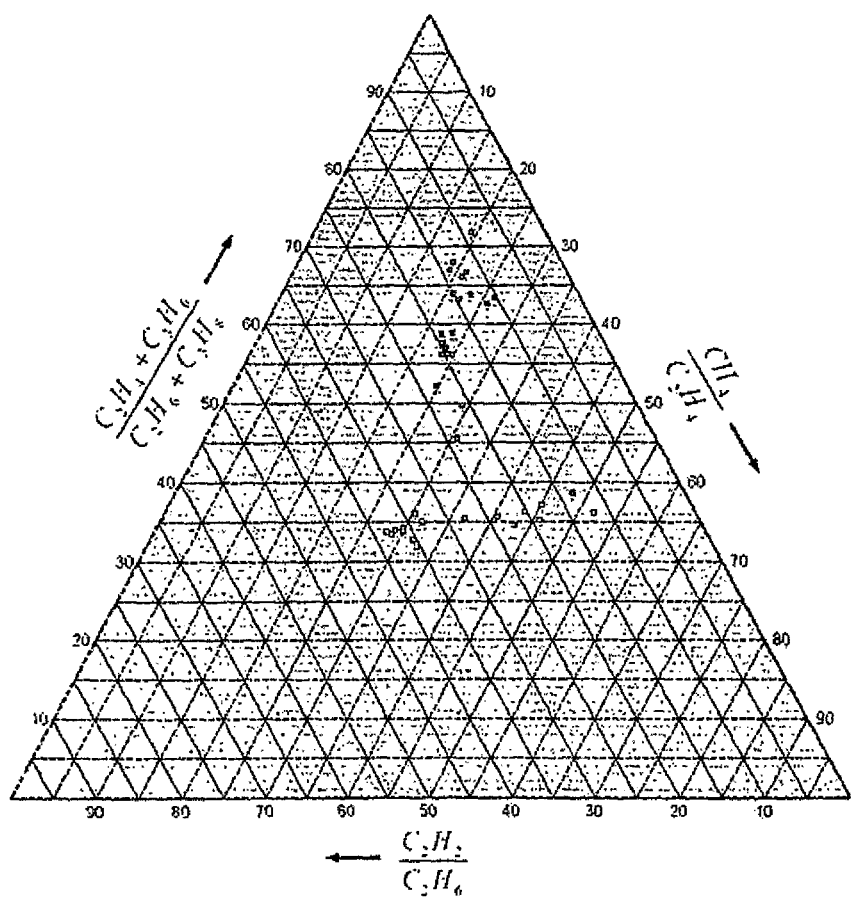

The method is described in more detail below by way of example with reference to drawings. In the drawing:

FIG. 1 shows a schematic flow diagram of a method according to the invention, FIG. 2 shows a first example of a trend evaluation, FIG. 3 shows a second example of a trend evaluation.

From the flow diagram of the method according to the invention for quantitatively analyzing gases shown schematically in FIG. 1, it can be seen that the gases that are suitable for purposes of monitoring the tap changer and that are therefore characteristic and allow an association and quantification of ageing effects, excessive discharge, and/or heating, are selected in a first method step. In this context, ageing effects are particularly understood to mean the ageing of oil due to excessive oxidation of the insulating oil used in the tap changer.

Three categories of possible fault gases have been shown to be particularly typical and therefore particularly usable for the method according to the invention. The characteristic gases can be categorized as follows:

The first category is formed by arc gases that are known per se, such as $H_2$ and $C_2H_2$, that occur in tap changers when the on-load changeover switch changes from the previous to the newly pre-selected winding tap of the variable-step transformer. These gases occur with all the changeover principles mentioned in the introduction albeit in different amounts. The next category of gases is thermal gases such as $CH_4$, $C_2H_6$, $C_2H_4$, $C_3H_8$ and $C_3H_6$ that form, for example, due to the heating of the tap changer transition resistors. The third and therefore last category of fault gases to be chosen includes oil ageing gases such as CO and $CO_2$ that are is basically also thermal gases, but allow conclusions to be drawn about the oil ageing state.

The concentration of the characteristic gases in the tap changer oil just described is measured at particular time intervals in a next method step. Examples of typical time intervals for the method are measurements twice a day, i.e. morning and evening. As an alternative to a time-based definition, a regular measurement of the characteristic gas concentration can also be based on the number of switching operations completed by the tap changer. An example of a typical interval would then be a measurement after 20 switching operations and every further multiple thereof.

When the derived gas concentrations are available, indicative quotients that allow direct conclusions about ageing effects, excessive discharge, and/or heating to be drawn therefrom are formed in a following method step. The quotients can be:

$CH_4/C_2H_4$ for ageing effects $C_2H_2/C_2H_6$ for discharges $(C_2H_4—C_3H_6)/(C_2H_6—C_3H_8)$ for heating.

A subsequent comparison of the currently derived value of each quotient with the most recently derived value of the same quotient shows a trend of the measured value development. If the value of each quotient remains approximately stable, then no warning is necessary and is consequently not output. If, however, one or even more quotients varies significantly, in particular in comparison with a plurality of previous values, that is to say over a longer period of time, then an appropriate warning is derived therefrom.

The characteristics of a further indicative quotient, namely $CO_2/CO$, for two tap changers under investigation is shown by way of example in FIG. 2 against the number of switching operations completed by the tap changers. Trends can be identified and analyzed and, if necessary warnings can be output in a particularly easy manner based on the resulting time curve.

FIG. 3 shows a triangular coordinate system that is known per se, such as is used as the "Duval Triangle" for example, however in a form that is further developed and is now suitable for purposes of monitoring the tap changer. Here, each side of the equilateral triangle represents an indicative quotient, shown in a relative percentage ratio to the sum of the values of all quotients. A point in this triangular representation is reached by determining and plotting the individual percentage values of the particular quotients for one and the same measurement on the correspondingly associated sides. Every point plotted is therefore defined by three coordinates. A statement regarding the trend is possible in this form of representation by determining and plotting further points for further measurements in the manner just described. If one or more measurements of the gas concentrations changes, the quotients consequently change and result in a characteristic shift of the points in the diagram that allows conclusions about the imminent fault to be drawn.

With the method according to the invention, it is therefore possible for the first time to make reliable statements about faults occurring on tap changers by means of gas analyses. Furthermore, it is possible to identify excessive mechanical wear or imminent faults at an early stage by assessing trends.

The invention claimed is:

1. In a method of quantitatively analyzing gases for on-load tap changers, the method comprising the following steps:

selecting characteristic arc gases including $H_2$ or $C_2H_2$, thermal gases including $CH_4$, $C_2H_6$ or $C_2H_4$, and oil-ageing gases including CO or $CO_2$ produced during the operation of the tap changer and that indirectly allow subsequent association and quantification of ageing effects, excessive discharge, or heating of the tap changer, measuring the concentration of the characteristic arc, thermal, and oil ageing gases in the oil at particular time intervals, forming indicative quotients from the measured concentrations of the characteristic arc, thermal, and oil-ageing gases that allow direct conclusions to be drawn about ageing effects, excessive discharge, or heating, displaying a trend by comparison of the currently derived value of each quotient with one or more of the most recently derived values of the same quotient, and deriving a warning for ageing effects, excessive discharge, and or heating if the corresponding quotients change significantly, the improvement wherein the thermal gases also include $C_3H_8$ or $C_3H_6$, the indicative quotient for the occurrence of discharges is the ratio $C_2H_2/C_2H_6$; and the indicative quotient for the occurrence of heating is $(C_2H_4+C_3H_6)/(C_2H_6+C_3H_8)$.

2. The method as claimed in claim 1, wherein the indicative quotients are displayed with respect to time.

3. The method as claimed in claim 1, wherein the indicative quotients are displayed with reference to the number of switching operations carried out by the tap changer.

4. The method as claimed in claim 1, wherein the indicative quotients are displayed in a relative percentage display in a triangular coordinate system.

* * * * *